United States Patent [19]

Pastan et al.

[11] Patent Number: 5,166,059
[45] Date of Patent: Nov. 24, 1992

[54] GENE THERAPY USING GENE FUSIONS FOR GENETIC OR ACQUIRED DISORDERS

[75] Inventors: Ira Pastan, Potomac; Michael Gottesman, Bethesda, both of Md.

[73] Assignee: The United States of America as represented by the Department of Health and Human Services, Washington, D.C.

[21] Appl. No.: 697,000

[22] Filed: May 3, 1991

Related U.S. Application Data

[63] Continuation of Ser. No. 202,783, Jun. 3, 1988, which is a continuation-in-part of Ser. No. 62,583, Jun. 16, 1987.

[51] Int. Cl.[5] .................. C12P 21/02; C12P 19/34; C12N 15/00; C12N 7/00
[52] U.S. Cl. .................. 435/69.7; 435/69.1; 435/91; 435/172.3; 435/235.1; 435/320.1; 435/240.2; 536/27; 530/350; 935/10; 935/32; 935/34; 935/57; 935/62; 935/70
[58] Field of Search .................. 435/69.1, 69.7, 91, 435/172.3, 235.1, 320.1, 240.2; 536/27; 570/350

[56] References Cited

U.S. PATENT DOCUMENTS 4,704,362  11/1987  Itakura et al. .................. 435/253

FOREIGN PATENT DOCUMENTS 0174810  3/1986  European Pat. Off. .

OTHER PUBLICATIONS

Gross et al., Proc. Natl. Acad. Sci. USA vol. 83 pp. 337-341 (1986).
Williams et al., Proc. Natl. Acad. Sci., USA, vol. 83, pp. 2566-2570 (1986).
Veda et al., Proc. Natl. Acad. Sci. vol. 84 pp. 3004-3008 (1987).

*Primary Examiner*—Joan Ellis
*Attorney, Agent, or Firm*—NIH/Division of Technology Transfer

[57] ABSTRACT

Gene therapy utilizing an MDR1 linked fusion coding sequence has been disclosed. ADA activity has been introduced into cells using MDR1 linked fusion gene.

8 Claims, 5 Drawing Sheets

GENE THERAPY USING GENE FUSIONS FOR GENETIC OR ACQUIRED DISORDERS

This is a continuation of application Ser. No. 07/202,783, filed Jun. 3, 1988 which in turn is: a continuation in part of application Ser. No. 07/062,583 filed Jun. 16, 1987. In application Ser. No. 07/062,583, the cloning of the human multidrug resistance gene (MDR1) and various applications thereof have been described. The disclosure contained herein is an extension of the basic concept set forth in the parent application Ser. No. 07/062,583 which is incorporated herein and made a part hereof by reference.

TECHNICAL FIELD

The present invention is related generally to the construction of fusion genes. More particularly, the present invention is related to the construction of a fusion gene comprising a coding sequence for a selectable marker linked by fusion to another coding sequence, the product of which is desired to be expressed in recipient cells.

BACKGROUND OF THE INVENTION

Development in recombinant DNA technology and the need to treat genetic disorders has led to the concept of "gene therapy." To this end, methods have been developed for the introduction and expression of foreign genes into somatic cells. However, a fusion gene per se as described herein has not heretofore been produced and the expression of the delivered gene in the recipient cell in accordance with the prevalent methods is usually found to be either very low or quite variable.

SUMMARY OF THE INVENTION

It is, therefore, an object of the present invention to provide an efficient and reproducibly reliable method of introducing genes into animal or human cells to treat genetic or acquired disorders or defects caused by enzyme deficiency.

It is a further object of the present invention to provide a selectable marker-linked fusion gene for transfer and expression of a desired gene in human cells without introducing a non-human antigen.

It is another object of the present invention to provide gene therapy for the treatment of severe combined immunodeficiency caused by adenosine deaminase (ADA) deficiency.

Other objects and advantages will become evident from the following detailed of the invention.

BRIEF DESCRIPTION OF THE DRAWINGS

These and other objects, features and many of the attendant advantages of the invention will be better understood upon a reading of the following detailed description when considered in connection with the accompanying drawings wherein: FIGS. 1 A,B,C schematically represent the construction of a retroviral expression vector pHaMDR1ADA which encodes a human P-glycoprotein-adenosine deaminase chimeric protein (it is noted that in FIGS. 1 A,B,C MDRADA represents MDR1ADA);

FIG. 2 shows Southern analysis of genomic DNAs of transfected KB cells Genomic DNA was digested with EcoRI, separated on a 0.7% agarose gel, transferred to nitrocellulose, and hybridized to a MDR 1-specific probe (pHDR5A). Panel A shows individually picked cell clones.

Lane 1: KB-A, mock-transfected, grown at 6 ng/ml colchicine.
Lane 2: KB-MDR1,A, pHaMDR1 transfected, grown at 6 ng/ml colchicine.
Lanes 3 and 4: KB-MDR1ADA-I, pHAMDR1A transfected, grown at 6 ng/ml (3) and 12 ng/ml (4) colchicine. Panel B shows pooled cell populations.
Lanes 1 and 2: pHaMDR1 transfected, grown at 6 ng/ml (1) and 24 ng/ml (2) colchicine.
Lanes 3 and 4: pHaMDR1ADA transfected, grown at 6 ng/ml (3) and 24 ng/ml (4) colchicine.
Lane 5: non-transfected parental KB-3-1 cell line, colchicine-sensitive;

FIG. 3 shows the results of immunoprecipitations of cell lysates. Cultures were labeled with $^{35}$S-methionine for 16 hours. Cell lysates were immunoprecipitated using anti-P-glycoprotein antiserum (lanes 1-7) or preimmune serum (lanes 8-12) and protein A sepharose. Fluorograms of the resulting SDS-polyacrylamide gels are shown. Arrows indicate the 170 kD P-glycoprotein (MDR1 gene product) and the 210 kD P-glycoprotein-ADA fusion protein (MDR1ADA).

Lane 1: drug-sensitive KB-3-1 control cell line, labelled and immunoprecipitated in parallel.
Lane 2: vinblastine-selected KB-V1 control cell line.
Lanes 3 and 8: pHaMDR1 transfected KB cell population grown at 24 ng/ml colchicine.
Lanes 4, 5, 9, 10: pHaMDR1ADA transfected KB cell populations grown at 6 ng/ml (4 and 9) and 24 ng/ml (5 and 10) colchicine.
Lanes 6, 7, 11, 12: pHaMDR1ADA transfected clone KB-MDR1ADA-I grown at 6 ng/ml (6 and 11) and 12 ng/ml (7 and 12) colchicine;
and FIG. 4 shows killing curves for control and pHaMDR1ADA cell lines. In each experiment 300 cells were plated in a 60 mm dish containing 5 ml culture medium supplemented with 1.1 mM adenosine, 1.0 mM uridine, 0.05 mM alanosine and variable amounts of 2'-deoxycoformycin After a growth period of ten days at 37° C. and 7% $CO_2$, cells were stained with methylene blue and colonies were counted.

(Δ) KB-A, mock-transfected clones.
(o) KB-MDR-A, pHaMDR1 transfected clone.
( ) KB-MDR1ADA-G, pHaMDR1ADA transfected clone..
(•) KB-MDR1ADA-I, pHaMDR1ADA transfected clone.

DETAILED DESCRIPTION OF THE INVENTION

The above and various other objects and advantages of the present invention are achieved by a chimeric gene comprising a selectable marker gene fused, linked or associated in tandem or otherwise with another gene, the expression of which is desired in the recipient cells.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The term "fusion gene" is defined herein as a DNA segment in which two or more genes are fused resulting in a single open reading frame for coding two or more proteins that as a result of this fusion are joined by one or more peptide bonds.

The concept of "gene therapy" utilizing the gene fusion expression system of the present invention is now exemplified by the construction, transfer and reliably efficient expression of the ADA gene simultaneously with a selectable marker gene such as the MDR1 gene, producing a bifunctional chimeric protein in the host cells.

The ADA gene was chosen for the illustrative purposes herein because adenosine deaminase (ADA; adenosine aminohydrolase; E.C. 3.5.4.4) deficiency is a genetic disorder which is associated with approximately one quarter of all cases of severe combined immunodeficiency (Hirschhorn, et al, 1979, *Clin. Immunol. Immunopathol,* 14:107). This disease is invariably fatal unless effectively treated. ADA catalyzes the irreversible deamination of adenosine and deoxyadenosine to inosine and deoxyinosine, respectively. Most ADA deficient patients produce a catalytically defective enzyme. As a consequence, the cytotoxic ADA substrates, adenosine and deoxyadenosine, as well as their metabolites. particularly deoxyadenosine 5'-triphosphate, are accumulated intracellularly. This leads to the specific destruction of T-lymphocytes and, to a lesser extent, B-lymphocytes, with consequent severe immunological dysfunction.

One of the therapies available for ADA deficiency is bone marrow transplantation from a normal histocompatible donor. However, for many patients, there are no suitable bone marrow donors. Alternative forms of treatment such as enzyme replacement by repeated erythrocyte transfusions or repeated intramuscular injection of polyethylene glycol-modified bovine ADA are also available, but these can lead to severe complications during long-term therapy.

Retrovirus-mediated transfer and expression of the ADA gene has been reported in a variety of human T and B lymphocyte cell lines, diploid human skin fibroblasts, as well as in murine NIH 3T3 and lymphoid cells. More recently, a Moloney murine leukemia virusbas ®d recombinant retrovirus has been used to express ADA in murine hematopoietic stem cells (Lim, et al, 1987, *Mol. Cell. Biol.* 7, 3459). Such retroviral constructs, however, contained no dominant marker gene which would allow selection and thus efficient enrichment of ADA expressing cells.

It is noteworthy that all recombinant retroviral constructs made so far carry, in addition to the ADA gene, a dominant selectable marker gene (e.g., neomycin phosphotransferase, hypoxanthine phosphoribosyl transferase or dihydrofolate reductase) and consistently expressed ADA in vitro, but failed to express ADA in vivo, i.e., in stem cells of experimental animals (Williams, et al, 1986, *Proc. Natl. Acad. Sci USA* 83, 2566; McIvor, et al, 1987, *Mol. Cell. Biol.* 7, 838; Zwiebel, et al, 1986, Blood 68, 307).

The present invention is the first to directly link the expression of the selectable marker gene (e.g., MDR1) to the expression of the ADA gene by creating a fusion MDR1-ADA gene which directs the synthesis of a bifunctional chimeric protein in the recipient cells of the host simultaneously conferring multidrug resistance and efficient ADA activity.

EXAMPLE 1

CONSTRUCTION OF A RETROVIRAL VECTOR CONTAINING A MDR1-ADA FUSION GENE

Figure 1A:
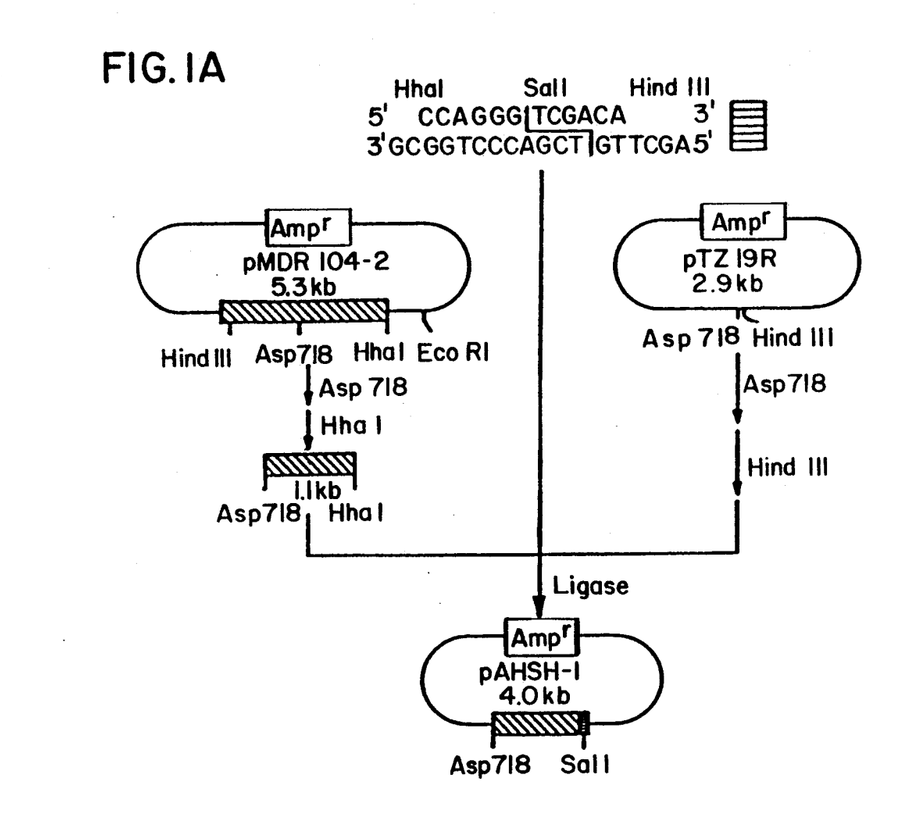

The cloning strategies for MDR1 related constructions have been fully described in application Ser. No. 07/062,583 which is incorporated herein by reference. Further strategies are now set forth. As shown schematically in FIG. 1, a human MDR1 cDNA was fused to a human ADA cDNA by a synthetic linker and placed between the 5' and 3' long terminal repeats (LTRs) of the Harvey murine sarcoma virus expression vector p006-HX following standard procedures such as described by Velu, et al, 1987, *Science* 238, 1408. All intermediate as well as the final constructs were characterized by restriction endonuclease mapping.

As a first step (FIG. 1A), a 1.1 kb Asp 718--- HhaI fragment encoding a carboxylterminal region of the MDR1 gene product P-glycoprotein (ranging from Val-926 to Lys-1278) was isolated from plasmid pMDR1 104-2. Two oligonucleotides, a 12-mer and an 18-mer, were synthesized and annealed to give an adapter With HhaI and HindIII compatible ends and containing a single SalI restriction site The adapter encodes the two carboxyl terminal amino acid residues of P-glycoprotein.

Figure 1B:
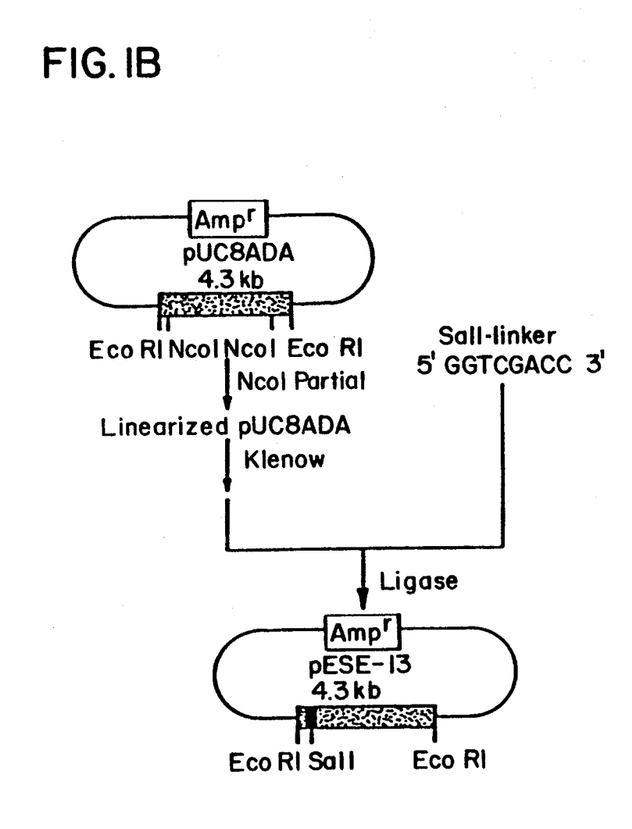

In a second step shown in FIG. 1B full-length human ADA cDNA corresponding to ADA 211 cDNA as described by Adrian, et al, 1984, *Hum. Genet.* 68, 169, Was subcloned as a 1.5 kb EcoRI fragment into the plasmid pUC8. Clone pUC8 ADA was then partially digested with NcoI to yield two types of linearized molecules which were both isolated by agarose gel electrophoresis. The desired linearized form of pUCS ADA was cleaved within the codon for the initiatormethionine of ADA. In order to restore this codon, the ends of the linearized plasmid were filled in using the Klenow fragment of DNA polymerase I. Then a nonphosphorylated SalI-linker [carrying the new amino acids (Arg-Pro) of the final tripeptide-junction between P-glycoprotein and ADA] was added by ligation and plasmic pESE-13 was obtained.

Figure 1C:
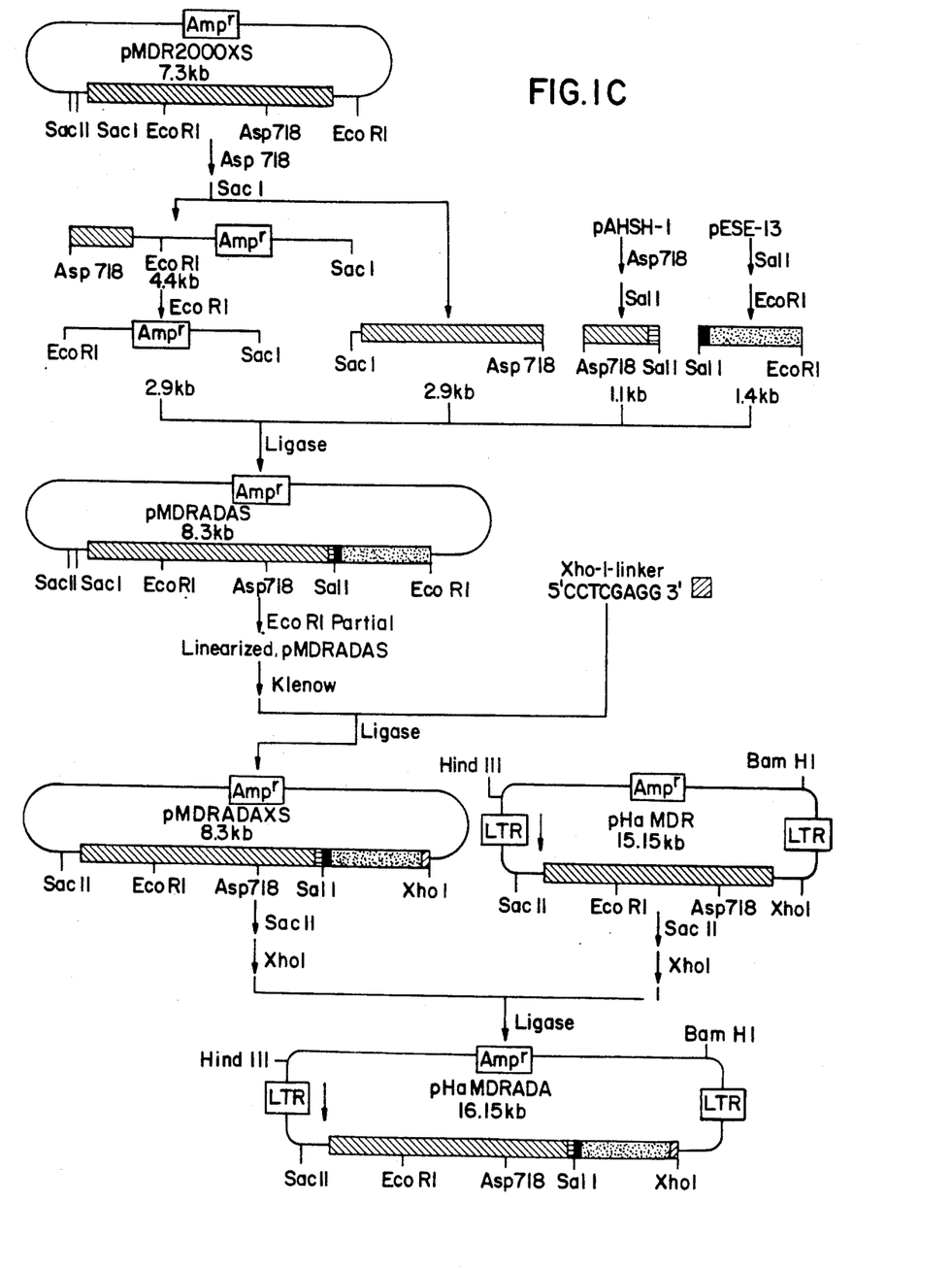

In the next step outlined in FIG. 1C, the human MDR1 and ADA genes were fused at the newly created single SalI site located at the 3' end of the P-glycoprotein coding region (pAHSH-1) and at the 5' end of the ADA structural gene (pESE-13). Concomitantly, the fusion gene was inserted into the pGEM-2 vector (Promega). To this end a 2.9 kb EcoRI—SacI fragment (containing pGEM-2 plasmid sequences) and a 2.9 kb SacI - Asp 718 fragment encoding the aminoterminal part of P-glycoprotein) were isolated from pMDR1 2000XS (Ueda, et al, 1987, *Proc. Natl. Acad. Sci. USA* 84, 3004) and ligated with a 1.1 kb Asp 718 -SalI fragment of pAHSH-1 (carrying the coding region for the carboxylterminal part of P-glycoprotein) and a 1.4 kb SalI - EcoRI fragment isolated from pESE-13 (containing the structural gene for ADA). In the resulting plasmid (pMDRADAS) a single SacII site was present at the 5' end of the fusion gene and could be used for its transfer into the retroViral expression vector pC06-HX (Velu, et al. 1987, *Science* 238, 1408).

For this purpose, however, a second site, a single XhoI site, had to be newly created at the 3' end of the fusion gene. Therefore, pMDRADAS was partially cut with EcoRI to linearize the molecule, filled in using the Klenow fragment of DNA polymerase I, and ligated with non-phosphorylated XhoI —linkers. The fusion gene was then excised from pMDRADA XS as a 5.45 kb SacII—XhoI fragment and ligated with the 10.7 kb SacII—XhoI fragment derived from pHaMDR1 and containing the retroviral vector sequences. The final construct is designated pHaMDR1ADA and carries the human MDR1-ADA fusion gene between the 5' and 8' LTRs of Harvey murine sarcoma virus. The MDR1-ADA fusion gene is the only functional eucaryotic gene in this vector and encodes a chimeric protein with an expected Mr of 210 kD. It consists of P-glycoprotein which is connected at the carboxyl-terminal amino acid Gln-1280 to the initiator-methionine of ADA by the tripeptide Gly-Arg-Pro.

A deposit of the pHaMDR1ADA has been made at the ATCC, Rockville, Md. on May 18, 1988 under the accession number 67699. The deposit shall be viably maintained, replacing it if it becomes non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

TRANSFECTION OF DRUG-SENSITIVE HUMAN KB CELLS AND COLCHICINE SELECTION

Drug-sensitive human KB-3-1 cells were transfected with pHaMDR1ADA DNA. Negative control cells received no DNA whereas positive control cells were transfected with pHaMDR1 which represents full-length human MDR1 DNA in the same Harvey murine sarcoma virus expression vector (see FIG. 1C). This plasmic represents full-length human MDR1 cDNA in the same Harvey murine sarcoma virus expression vector (see FIG. 1C). This plasmid confers the full phenotype of multidrug resistance to a variety of mouse and human cell lines as mentioned in application Ser. No. 07/062,583.

Plasmid DNA used for cell transfections was isolated by standard alkaline lysis followed by cesium chloride gradient centrifugation. Drug-sensitive human KB-3-1 cells were transfected by the standard calcium phosphate precipitation method. 10 $\mu$g of plasmid DNA were used to transfect $5 \times 10^5$ cells per 10 cm dish. Sixteen hours after transfection cells were washed twice and 24 hrs later they were split 1:5 into medium containing the selective drug colchicine at a concentration of 6 ng/ml. After a growth period of ten days, two dishes of cells were stained with 0.5% (w/v) methylene blue in 10% (v/v) ethanol and individual colonies counted. The data presented in Table I show the relative transfection efficiencies of plasmids pHaMDR1ADA and pHaMDR1.

From three non-stained dishes six individual colchicine-resistant colonies were picked and representative cell pools were collected. Both individual clones and cell populations were grown for at least ten more days in the presence of 6 ng/ml colchicine. It has been shown that due to amplification of the endogenous MDR1 gene, human multidrug resistant cell lines become increasingly drug resistant when the concentration of the selective drug in the growth medium is raised. Hence, to investigate whether the transferred MDR1 or MDR1ADA DNA sequences are also amplified, the concentration of colchicine in the culture medium of transfected cells was raised stepwise in twofold increments up to 96 ng colchicine/ml. Both individual clones and cell populations were passaged twice in appropriate drug concentrations before being plated in the next higher concentration. No difference in growth rate at any concentration of colchicine was observed between pHaMDR1 and pHaMDR1ADA transfected KB cells, indicating that the ADA fusion does not affect the functional activity of P-glycoprotein in the chimeric protein.

GENOMIC DNA ANALYSIS OF TRANSFECTED KB CELLS

Figure 2A:
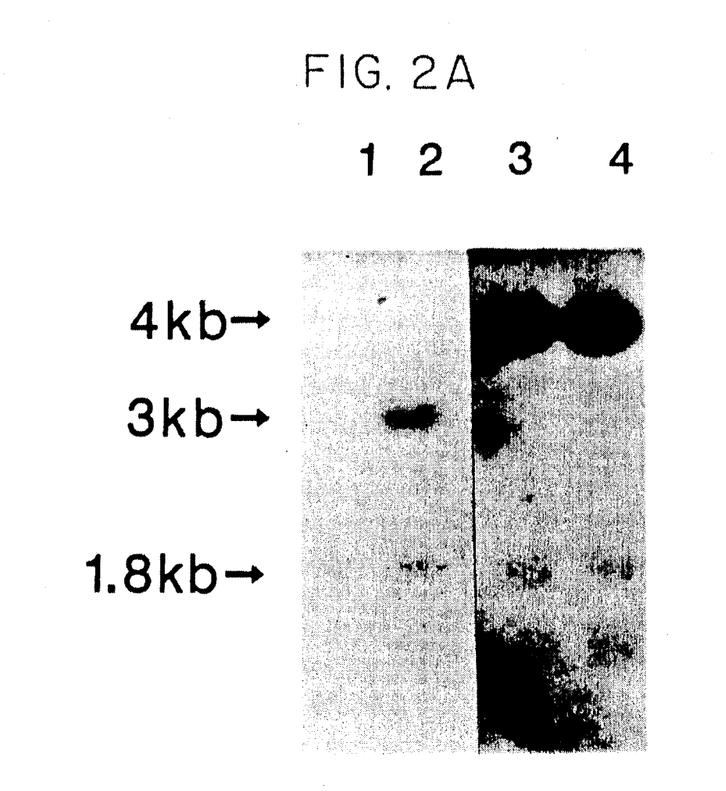
Figure 2B:
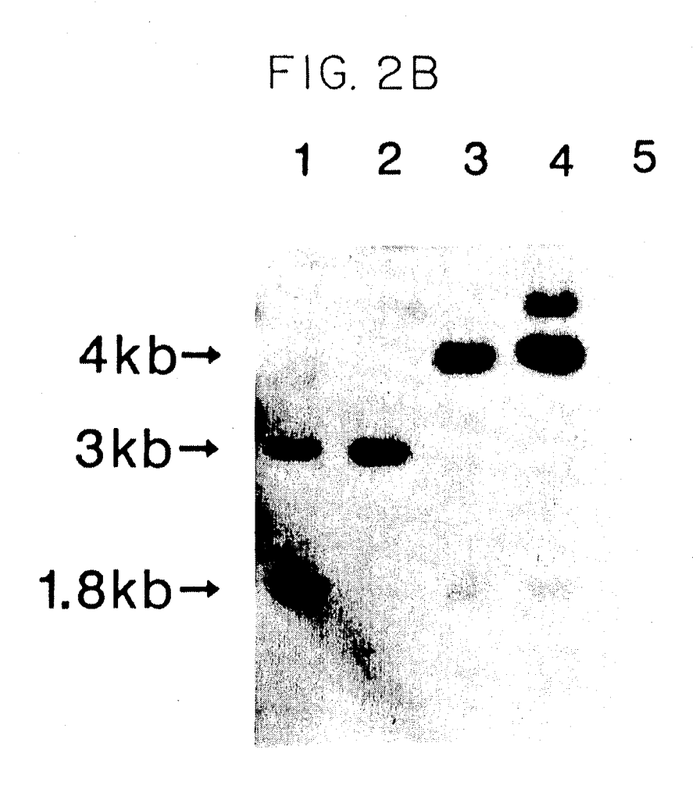

In order to confirm the presence of the introduced MDR1 or MDR1ADA genes and to investigate their copy number, genomic DNA was isolated from transfected and control KB cells by standard procedures (Chen, et al, 1986, Cell 47, 381). Equal amounts of genomic DNA were analyzed by restriction endonuclease digestion using EcoRI, followed by agarose gel electrophoresis, Southern transfer and hybridization to a MDR1-specific probe. A 3 kb fragment of pHaMDR1 transfected cells and a 4 kb fragment of pHaMDR1ADA transfected cells were expected to give rise to a hybridization signal. Indeed, as shown in FIG. 2, strong hybridization signals of the correct size were obtained both for transfected individual clones and cell populations indicating that the integrated DNA sequences were intact. A weak 1.8 kb hybridization signal was detected in all investigated cells including the parental KB-3-1 cell line and a mock-transfected KB clone. Without being bound to any theory, it is postulated that this signal is probably derived from the endogenous single-copy MDR1 gene. The intensity of the 3 kb and 4 kb hybridization signals indicate that the pHaMDR1 and pHaMDR1 ADA transfected cells contain multiple copies of the introduced DNA sequences. However, from the data presented in FIG. 3, it cannot be definitively concluded whether increasing concentrations of colchicine in the culture medium caused further amplification of the introduced DNA sequences. The apparent amplification in the cell populations (FIG. 2B, lanes 2 and 4) could simply be a reflection of an enrichment for cells which express high levels of the MDR1 or MDR1ADA gene even at low concentrations of colchicine. Moreover, a potential rearrangement of the introduced DNA sequences in pHaMDR1 ADA transfected cells (FIG. 2B, lane 4) is also possible.

ANALYSIS OF THE PROTEINS PRODUCED BY TRANSFECTED KB CELLS

Figure 3:
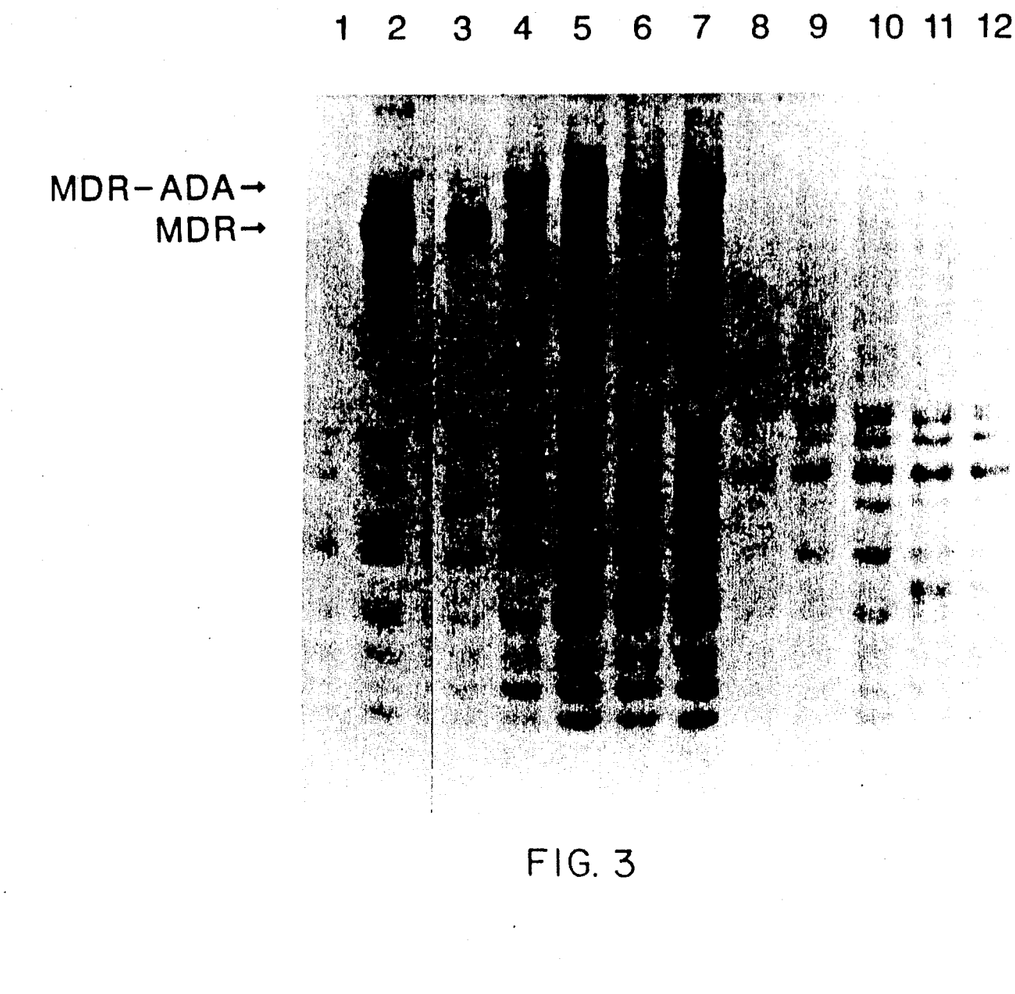

Having confirmed the presence of the introduced DNA sequences in pHaMDR1 ADA and pHaMDR1 transfected KB cells, it was important to investigate their expression. To this end immunoprecipitations using a polyclonal rabbit antiserum against the carboxyl terminal regions of P-glycoprotein were performed. Cell cultures were radiolabeled with [$^{35}$S]-methionine for 16 hours and cell lysates prepared. Antigen-antibody complexes were allowed to form for 18 hours at 4° C. and were then precipitated with Protein A Sepharose. The precipitated proteins were analyzed by electrophoresis on a SDS —7% polyacrylamide gel followed by fluorography. As shown in FIG. 3, P-glycoprotein with a Mr of 170 kD was detected in pHaMDR1 transfected cells. The immunoprecipitated protein from pHaMDR1ADA transfected cells has a higher Mr which is in good agreement with the calculated Mr of 210 kD of the MDR1 ADA fusion protein. Furthermore, the levels of the chimeric protein seem to increase along with the colchicine resistance of the cells.

ANALYSIS OF ADA ACTIVITY IN TRANSFECTED KB CELLS

Figure 4A:
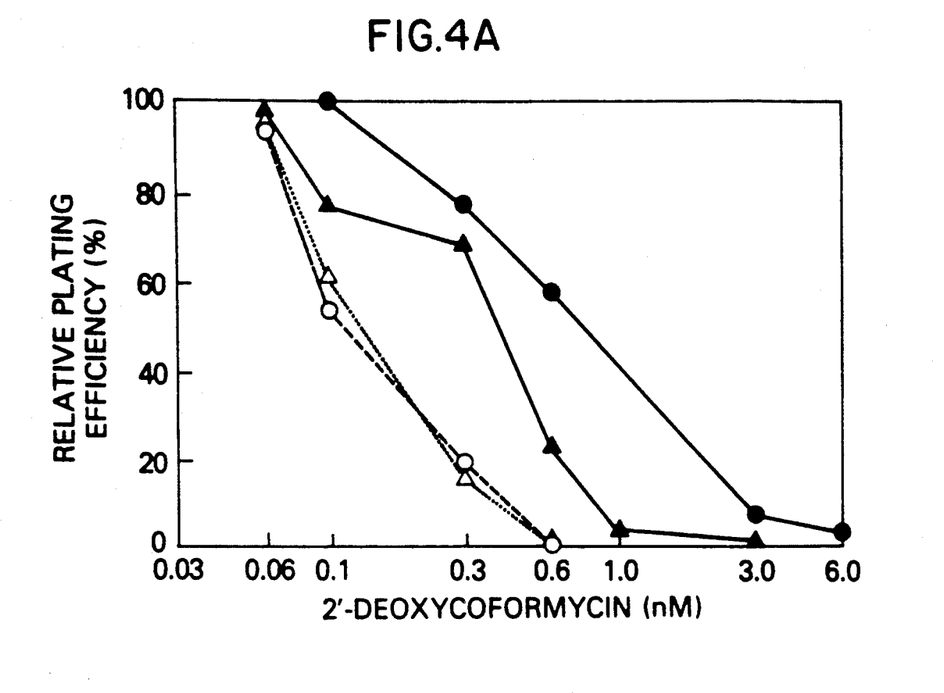
FIG. 4A shows individual clones selected at 6 ng/ml colchicine.
Figure 4B:
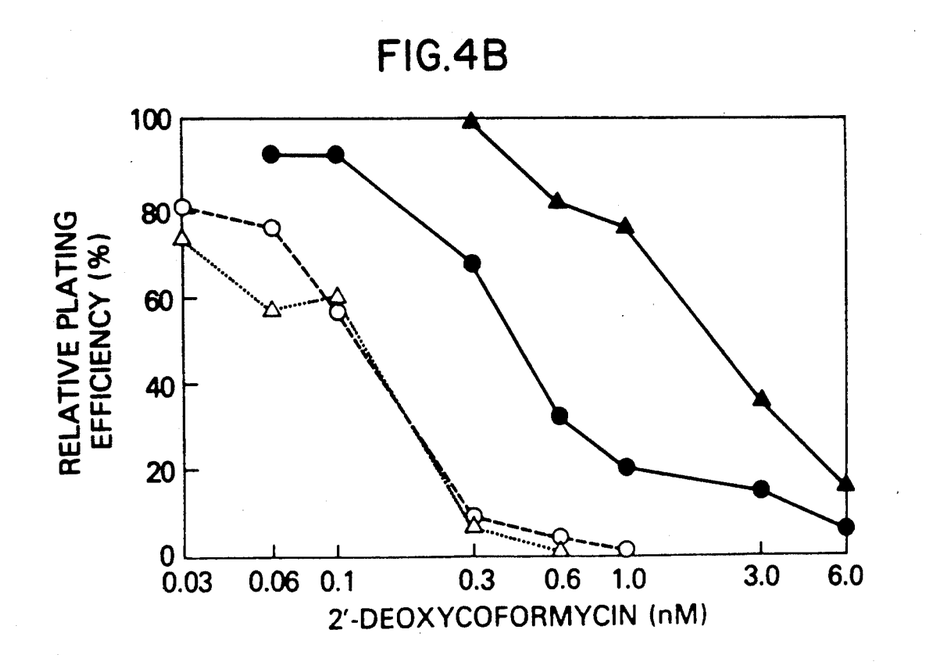
FIG. 4B shows collected cell populations grown at 16 ng/ml (circles) and 24 ng/ml (triangles) colchicine. Dashed lines and open symbols (o,Δ) represent pHaMDR1 transfected cells, and solid lines and closed symbols (o, ) are pHaMDR1ADA transfected cells.

After the expressed MDR1 ADA fusion protein was demonstrated to be intact, it was essential to test whether the ADA part was functionally active. To demonstrate ADA function, the sensitivity of pHaMDR1ADA transfected cells to 2'-deoxycoformycin (dCF) was investigated in the presence of toxic concentrations of adenosine and compared to the sensitivity of pHaMDR1 transfected cells. dCF is a tight-binding transition-state analog inhibitor of ADA ($Dd = 2.5 \times 10^{-12}$, Agarwal, et al, 1977, *Biochem. Pharmacol.* 26, 359; Frieden, et al, 1980, *Biochemistry* 19, 5303). Under conditions where ADA activity is required (such as in the presence of cytotoxic amounts of adenosine) dCF can be used to estimate intracellular ADA levels. The amounts of dCF necessary to inhibit cell growth correlated with the amounts of functional ADA. Killing curves were performed by growing a constant number of cells (initially 300 cells were plated in a 60 mm dish) in culture medium supplemented with 1.1 mM adenosine, 1.0 mM uridine. 0.05 mM alanosine and variable amounts of dCF. Alanosine was added to block de novo AMP synthesis and uridine to alleviate the block in UMP synthesis caused by the high adenosine concentration. After incubation at 37° C. in 7% $CO_2$ for 10 days, the cells were stained with 0.5% (w/v) methylene blue in 50% (v/v) ethanol and colonies were counted. The results are presented in FIG. 4 and $ID_{50}$ values are shown in Table II. The $ID_{50}$ value corresponds to the concentration of dCF which reduces plating efficiency to 50% of the control without dCF. The data clearly indicate that pHaMDR1 ADA transfected cells survive higher concentrations of dCF than pHaMDR1 transfected cells or mock-transfected control cells. Hence, it is concluded that ADA, as part of the chimeric MDR1-ADA fusion protein, is functional. Evidence for enzymatic activity, located primarily in the membrane fraction of transfected cells, is shown in Table III.

It should be noted that MDR1 is only an example of a selectable marker gene. Given the illustrative methodology described herein, of course any selectable marker gene can be similarly employed to produce a chimeric gene. Furthermore, the linked gene which is introduced by fusion with the selectable marker gene may be altered (for example by mutation) and the effect of such alterations determined in intact living cells. Such manipulations allow the determination of the effect of the alteration and the verification that the mutant gene is in fact introduced and expressed as a polypeptide. In the current example, the human MDR1 gene linked to the ADA gene could be used to introduce mutant ADA proteins into cells for determining the function of different parts of the ADA molecule. Since ADA is also a selectable marker gene in tissue culture cells via the deoxycoformycin selection, ADA can be used as the selectable marker to introduce an altered MDR1 gene into cells thereby allowing the determination of the function of various modifications of the MDR1 protein.

It is understood that the examples and embodiments described herein are for illustrative purposes only and that various modifications or changes in light thereof will be suggested to persons skilled in the art and are to be included within the spirit and purview of this application and scope of the appended claims.

TABLE I

Transfections of human KB-3-1 cells with pHaMDR1ADA and pHaMDR1

| DNA (amount) | Colonies/$5 \times 10^5$ cells |
| --- | --- |
| pHaMDR1ADA (5 μg) | 75 |
| pHaMDR1ADA (10 μg) | 125 |
| pHaMDR1 (5 μg) | 330 |
| pHaMDR1 (10 μg) | 550 |
| no DNA | 5 |

KB-3-1 cells were plated at $5 \times 10^5$ cells/10 cm dish and transfected the next day with the indicated DNAs. After 2 days cells were trypsinized and split 1:5 into culture medium supplemented with 6 ng/ml colchicine. Ten days later colonies were stained with methylene blue and counted.

TABLE II

Sensitivity of transfected KB cell lines to 2'-deoxycoformycin in the presence of toxic concentrations of adenosine

| Cell Line | DNA Used for Transfection | Colchicine Concentration of Selection (ng/ml) | $ID_{50}$ Value (nM dCF) |
| --- | --- | --- | --- |
| KB-A | None | 6 | 0.13 |
| KB-MDR1-A | pHaMDR1 | 6 | 0.11 |
| KB-MDR1ADA-G | pHaMDR1ADA | 6 | 0.40 |
| KB-MDR1ADA-I | pHaMDR1ADA | 6 | 0.80 |
| KB-MDR1 Pool | pHaMDR1ADA | 6 | 0.13 |
| KB-MDR1 Pool | pHaMDR1 | 24 | 0.11 |
| KB-MDR1ADA Pool | pHaMDR1ADA | 6 | 0.42 |
| KB-MDR1ADA Pool | pHaMDR1ADA | 24 | 2.0 |

KB-A, KB-MDR1, KB-MDR1ADA G, and KB-MDR1ADA I are individual clones.

TBLE III

ADA ACTIVITY OF CRUDE MEMBRANE AND CYTOSOLIC
FRACTIONS OF PARENTAL AND TRANSFECTED KB CELL LINES

| Cell line | DNA Used for Transfection | Colchicine Concentration for Selection (nm/ml) | ADA Activity (nmol Inosine/min/mg) | |
|---|---|---|---|---|
| | | | Cytosol | Membranes |
| KB-3-1 | None | 0 | 18.2 | 3.0 |
| KB-MDR1 Pool | pHaMDR1 | 6 | 13.6 | 2.0 |
| KB-MDR1 Pool | pHaMDR1 | 48 | 15.6 | 1.8 |
| KB-MDR1ADA Pool | pHaMDR1ADA | 6 | 15.8 | 1.9 |
| KB-MDR1ADA Pool | pHaMDR1ADA | 24 | 13.3 | 94.9 |
| KB-MDR1ADA Pool | pHaMDR1ADA | 48 | 17.1 | 153.4 |

ADA assays were performed according to Yeung, C.-y., Ingolia, D. E., Bobonis, C., Dunbar, B. S., Riser, M. E., Siciliano, M. J., and Kellems, R. E. (1983) *J. Biol. Chem.* 258, 8338–8345. To determine ADA activity in the membrane or cytosolic fraction, cells were collected by scraping into PBS, washed twice with PBS, resuspended in hypotonic lysis buffer (10 mM Tris HCl pH 7.5, 10 mM NaCl, 1 mM $MgCl_2$) at a concentration of $2 \times 10^7$ cells/ml and incubated in an ice-bath for 15 min. The swollen cells were disrupted with 20 strokes in a tightly fitting Dounce homogenizer and the nuclei removed by centrifugation at $400 \times g$ for 10 min at 4° C. The Pellet obtained by subsequent centrifugation at $30,000 \times g$ for 30 m in at 4° C. was used as the crude membrane fraction and the supernatant was used as the cytosolic fraction.

What is claimed is:

1. A nucleotide sequence encoding an MDR1-ADA fusion gene comprising the coding sequence for the human MDR1 gene directly linked to the 5' end of the coding sequence for the ADA gene, wherein the linked coding sequences form a single open reading frame.

2. An expression vector comprising the fusion gene of claim 1.

3. An expression vector having the identifying characteristics of ATCC 67699.

4. The expression vector of claim 2, wherein said expression vector is a retroviral vector.

5. The expression vector of claim 4 wherein said vector further comprises the Harvey sarcoma viral LTR promoter operably linked to the nucleotide sequence encoding the MDR1-ADA fusion protein.

6. A mammalian cell transfected with the vector of claim 2.

7. A method for expression the MDR1-ADA fusion gene which comprises culturing the mammalian cells of claim 6 under suitable conditions so that the MDR1-ADA fusion protein is produced by said cells.

8. The method of claim 7 wherein said cells are cultured in the presence of a stimulatory drug under conditions that result in amplification of the MDR1-ADA fusion protein.

* * * * *